United States Patent
Wulfman et al.

(10) Patent No.: US 10,537,669 B2
(45) Date of Patent: Jan. 21, 2020

(54) INTERVENTIONAL CATHETERS HAVING CUTTER ASSEMBLIES AND DIFFERENTIAL CUTTING SURFACES FOR USE IN SUCH ASSEMBLIES

(71) Applicant: BOSTON SCIENTIFIC LIMITED, Hamilton (BM)

(72) Inventors: Edward I. Wulfman, Woodinville, WA (US); Casey Torrance, Snohomish, WA (US)

(73) Assignee: BOSTON SCIENTIFIC LIMITED (BM)

( * ) Notice: Subject to any disclaimer, the term of this patent is extended or adjusted under 35 U.S.C. 154(b) by 227 days.

(21) Appl. No.: 15/485,837

(22) Filed: Apr. 12, 2017

(65) Prior Publication Data

US 2017/0215914 A1 Aug. 3, 2017

Related U.S. Application Data

(63) Continuation of application No. 14/508,731, filed on Oct. 7, 2014, now Pat. No. 9,656,008, which is a (Continued)

(51) Int. Cl.
*A61B 17/32* (2006.01)
*A61M 1/00* (2006.01)
(Continued)

(52) U.S. Cl.
CPC ....... *A61M 1/0084* (2013.01); *A61B 1/00087* (2013.01); *A61B 1/05* (2013.01);
(Continued)

(58) Field of Classification Search
CPC .............. A61M 1/0058; A61M 1/0023; A61M 1/0066; A61M 5/142; A61M 5/16831; A61M 25/0082; A61M 25/09; A61M 1/0084; A61B 17/3207; A61B 17/320758; A61B 2017/320775; A61B 2217/005; A61B 2217/007; A61B 1/00087; A61B 1/05; A61B 8/12; A61B 8/445; A61B 17/32002; A61B 17/320725; A61B 2017/22079; A61B 2017/320004; A61B 2017/320032
See application file for complete search history.

(56) References Cited

U.S. PATENT DOCUMENTS 3,922,190 A 11/1975 Cowan
4,445,509 A 5/1984 Auth
(Continued)

FOREIGN PATENT DOCUMENTS

WO 2004080345 A2 9/2004
WO 2004080507 A2 9/2004

*Primary Examiner* — George J Ulsh
(74) *Attorney, Agent, or Firm* — Seager, Tufte & Wickhem LLP (57) ABSTRACT

A rotatable operating head for removal of obstructive material from a target site in a body lumen or cavity is operably connected to a rotatable, translatable drive shaft that is driven by a drive motor and received through an elongated catheter. The operating head includes a plurality of differential cutting blades, with at least one of the cutting blades being a stepped blade, the stepped blade comprising a raised cutting surface positioned adjacent, or in proximity to, a shoulder region.

20 Claims, 5 Drawing Sheets

Related U.S. Application Data continuation of application No. 11/866,967, filed on Oct. 3, 2007, now Pat. No. 8,852,219.

(60) Provisional application No. 60/894,173, filed on Mar. 9, 2007, provisional application No. 60/828,209, filed on Oct. 4, 2006.

(51) Int. Cl.

| | | |
|---|---|---|
| *A61B 17/3207* | (2006.01) | |
| *A61B 1/00* | (2006.01) | |
| *A61B 1/05* | (2006.01) | |
| *A61B 8/12* | (2006.01) | |
| *A61B 8/00* | (2006.01) | |
| *A61M 25/09* | (2006.01) | |
| *A61M 5/142* | (2006.01) | |
| *A61M 5/168* | (2006.01) | |
| *A61M 25/00* | (2006.01) | |
| *A61B 17/22* | (2006.01) | |

(52) U.S. Cl.
CPC .............. *A61B 8/12* (2013.01); *A61B 8/445* (2013.01); *A61B 17/32002* (2013.01); *A61B 17/3207* (2013.01); *A61B 17/320725* (2013.01); *A61B 17/320758* (2013.01); *A61M 1/0023* (2013.01); *A61M 1/0058* (2013.01); *A61M 1/0066* (2013.01); *A61M 5/142* (2013.01); *A61M 5/16831* (2013.01); *A61M 25/0082* (2013.01); *A61M 25/09* (2013.01); *A61B 2017/22079* (2013.01); *A61B 2017/320004* (2013.01); *A61B 2017/320032* (2013.01); *A61B 2017/320775* (2013.01); *A61B 2217/005* (2013.01); *A61B 2217/007* (2013.01)

(56) References Cited

U.S. PATENT DOCUMENTS

| | | |
|---|---|---|
| 4,657,017 A | 4/1987 | Sorochenko |
| 4,715,256 A | 12/1987 | Kunze et al. |
| 4,790,813 A | 12/1988 | Kensey |
| 5,042,984 A | 8/1991 | Kensey et al. |
| 5,097,849 A | 3/1992 | Kensey et al. |
| 5,516,242 A | 5/1996 | Andronica |
| 5,759,185 A | 6/1998 | Grinberg |
| 5,913,867 A | 6/1999 | Dion |
| 5,947,989 A | 9/1999 | Shikhman et al. |
| 6,001,112 A | 12/1999 | Taylor |
| 6,063,069 A | 5/2000 | Cragg et al. |
| 6,282,797 B1 | 9/2001 | Osada et al. |
| 6,503,261 B1 | 1/2003 | Bruneau et al. |
| 6,550,702 B2 | 4/2003 | Champlin |
| 6,565,588 B1 | 5/2003 | Clement et al. |
| 6,666,874 B2 | 12/2003 | Heitzmann et al. |
| 6,818,001 B2 | 11/2004 | Wulfman et al. |
| 6,889,420 B2 | 5/2005 | Jones |
| 7,344,546 B2 | 3/2008 | Wulfman et al. |
| 2002/0007190 A1 | 1/2002 | Wulfman et al. |
| 2002/0143350 A1 | 10/2002 | Heitzmann et al. |
| 2004/0006358 A1 | 1/2004 | Wulfman et al. |
| 2004/0220519 A1 | 11/2004 | Wulfman et al. |
| 2005/0216019 A1 | 9/2005 | Eckman |
| 2008/0228208 A1 | 9/2008 | Wulfman et al. |

FIG. 7

INTERVENTIONAL CATHETERS HAVING CUTTER ASSEMBLIES AND DIFFERENTIAL CUTTING SURFACES FOR USE IN SUCH ASSEMBLIES

REFERENCE TO PRIORITY APPLICATIONS

This application is a continuation of U.S. patent application Ser. No. 14/508,731, filed Oct. 7, 2014, which is a continuation of U.S. patent application Ser. No. 11/866,967, filed Oct. 3, 2007, now U.S. Pat. No. 8,852,219; which claims priority to U.S. provisional patent application Nos. 60/894,173 filed Mar. 9, 2007, and 60/828,209 filed Oct. 4, 2006. The disclosures of which are incorporated by reference herein in their entireties.

FIELD OF THE INVENTION

The present invention relates to methods and systems for removing material, such as obstructions and partial obstructions, from an internal lumen or cavity of a mammalian subject, such as a blood vessel. More particularly, the present invention relates to interventional catheters having rotating operating heads incorporating blade structures for removing obstructions and partial obstructions from a lumen or cavity.

BACKGROUND OF THE INVENTION

Removal of disease such as atherosclerotic plaque, thrombus and other types of obstructions and partial obstructions from internal body lumens or cavities using advanceable, rotating operating heads is a well-established interventional technique. Numerous interventional catheters have been conceived and developed. Most of these systems require placement of a guiding catheter and guide wire prior to introduction of the interventional catheter and placement of the interventional catheter at the target operating site. Many of these prior art systems incorporate mechanical aspiration systems to remove fluid and particulates from the site, and some systems incorporate or are used in conjunction with other mechanisms such as distal filters for preventing removed material from circulating in the blood stream.

Despite the many and varied approaches to material removal systems, many challenges remain in providing systems for removing material from a lumen, such as a blood vessel, safely and reliably and without causing complications. The safety and reliability of the system is manifestly critical. Recovery of debris generated during a material removal operation, or reducing the size of the debris to a particle size that will not produce blood vessel damage or embolic events, is essential. The flexibility and size of an interventional catheter are also important features. The system must be small enough and flexible enough to navigate through sometimes tortuous internal structures and passageways, such as blood vessels, for placement at the target interventional site. The interventional catheter must also have sufficient integrity and a combination of stiffness and flexibility to operate reliably at high rotational rates while allowing for aspiration of fluids from the site and/or infusion of fluids to the site.

In interventional catheters that employ a "cutting head," any cutter structures must be benign or retained in a protective sheath during navigation of the operating head to and from the interventional target site, yet effectively remove material during the operation. In addition, cutter structures must effectively remove disease or undesired material without damaging delicate neighboring tissue, such as blood vessel walls or other healthy tissue, which often surrounds and may be attached to the undesired material. Thus, it is important for cutter structures of interventional catheters to accurately and reliably differentiate between the diseased or undesired material and healthy tissue.

Differential cutting blades exert high shear forces against relatively hard substrates to cut or ablate relatively hard, inelastic, material. Softer, elastic structures, such as healthy tissue, blood vessel walls and the like, are deformed and displaced rather than cut by differential cutting blades, thereby reducing the shear forces and protecting elastic structures from damage. Less elastic material does not deform when contacted by a differential cutting blade, and shear stresses are consequently exerted on less elastic material to cut or scrape the material without damaging elastic tissue in proximity. In this manner, fragments of diseased, undesirable material are removed by differential cutting blades, while the more elastic, healthy tissue remains undamaged.

U.S. Pat. No. 4,445,509 describes differential cutting in the context of an atherectomy device. This patent describes a cutter assembly having a plurality of cutting flutes, each cutting flute having a blade surface operating according to the principle of differential cutting. Aspiration ports are provided in the body of the cutter assembly for collection and removal of particulates and liquids from the site of the intervention. U.S. Patent Publication 2004/0006358 A1 also discloses differential cutting surfaces forming an acute angle of attack with respect to the occlusive material. Aspiration ports are provided between the cutting surfaces.

Some interventional catheters use diamond grit on a cutting surface in an effort to provide highly divided, small particle size debris. Diamond grit particles, however, do not operate as differential cutters except in their smallest embodiment because, depending on their orientation on the cutting surface, their exposed surfaces form random cant angles producing different cutting characteristics at different points of contact with tissue. Relatively coarse diamond grit can act as a differential cutter because of the ratios of diamond size and population to tissue flexibility, but typically is more likely to damage elastic, healthy tissue such as blood vessel walls. Relatively fine diamond grit has slow material removal rates, requiring the use of higher rotational speeds. The use of grit or abrasive particles or surfaces is, however, beneficial in many applications.

The extent and consistency of the disease or undesired material forming an obstruction are frequently not well characterized prior to the intervention. Thus, although interventional catheters and cutter assemblies having different sizes and material removal properties may be provided, and may even be interchangeable on a material removal system, it is difficult to ascertain which combination of features will be most effective in any particular intervention prior to insertion of the device. Various quick-connect systems have been developed to permit removal and installation of multiple operating catheters during a single surgical intervention. Interchange, withdrawal and insertion of multiple interventional catheters, however, is time consuming, and may result in increased blood loss and increased risk to the patient.

Providing access to multiple cutter assemblies having different sizes and different material removal properties on a single interventional operating catheter is highly desirable. Interventional catheters having cutter or material removal assemblies that can be operated to vary the size of the cutting profile at the material removal site are known. Cutter assemblies comprising a distal cutter assembly having fixed blades and a proximal cutter assembly having pivoting blades are described, for example, in U.S. Pat. Nos. 6,565,588 and 6,818,001.

Several prior art interventional catheters provide for aspiration of liquids and/or debris from the material removal site. Numerous interventional catheters also provide infusion of a liquid to the site of the intervention. Infused liquids may assist in the material removal process, or may be used to deliver diagnostic, imaging or therapeutic materials prior to, during or following an intervention.

Although interventional catheters are used frequently, limitations in the flexibility, reliability and versatility, together with capability of use and performance of existing systems limit the types of disease conditions that can be effectively treated.

There thus remains a need for improved interventional catheter assemblies.

SUMMARY OF INVENTION

The present invention provides interventional catheters that may be employed to rapidly and effectively remove unwanted material from body lumens or cavities. Interventional catheters and control systems disclosed herein may be adapted for use within a variety of body lumens or cavities such as blood vessels and vascular cavities, gastrointestinal cavities, lumens or cavities in the urinary system and in male and female reproductive organs, and other fluid cavities such as pulmonary lumens and gas exchange cavities, nasal and sinus cavities, and the like. The lumen or cavity may form a generally tubular structure, such as a blood vessel, a ureter, a fallopian tube, a nasal passageway, and other tubular passageways. For example, systems of the present invention may be used for removing undesired material from native blood vessels such as native coronary, renal, cranial, peripheral and other blood vessels, artificial or grafted vessels such as saphenous vein grafts, and the like. The lumen may have implanted devices such as stents in place. The lumen or cavity may be within, or in proximity to, an organ such as a kidney, gall bladder, lung or the like, or the body cavity may form part of another system, such as a lymph node, spinal canal, or the like. Interventional catheters are generally used to remove unwanted material from a target site in body lumens or cavities of mammalian subjects, particularly human patients.

The undesired material that is removed using interventional catheter assemblies and control systems disclosed herein may be disease material such as atherosclerotic plaque, calcified plaque, thrombus, or other types of deposits, gallstones, a valve or portion thereof, and the like. In certain embodiments, the interventional catheter assemblies disclosed herein are employed in the treatment of cardiovascular or peripheral artery disease (PAD) to remove disease material from blood vessels, including peripheral blood vessels.

The present interventional catheter assembly includes a catheter system that is at least partially inserted and navigated within a patient's body while an operator controls the system externally of the catheter system. The interventional catheters disclosed herein incorporate a material removal component, referred to herein as an "operating head," which is generally positioned at or near the distal end of the interventional catheter system. As used herein, "proximal" refers to a direction toward the system controls and the operator along the path of the catheter system, and "distal" refers to the direction away from the system controls and the operator along the path of the catheter system toward or beyond a terminal end of the operating head.

Fluidic communication between the operating head and externally positioned components of the interventional catheter system is generally provided by one or more sealed passageways of the catheter system. Other types of communication systems or pathways may also be provided for delivery of power, for rotationally driving and translating the operating head, for implementing various control features, and the like. The operating head may be driven, or controlled, using electrical systems, radio frequency and other remote control systems, mechanical systems, magnetic systems and other systems or modalities suitable for remote operation of an operating head. The operating head may also incorporate features providing additional functionalities such as ultrasound guidance, various types of imaging features, and the like. The system components described below are described as exemplary components and are not intended to limit the scope of the invention.

The interventional catheter system may be used in conjunction with a flexible guidewire that is navigated through internal pathways, such as blood vessels, to a target material removal site. For partial obstructions, the guidewire is generally placed across the lesion and the operating head of the interventional catheter is advanced on the guidewire to the target site and then into and through the lesion. When a lumen is totally obstructed and a guidewire cannot penetrate the obstruction without causing harm to nearby tissue or risking embolization, the operating head may be advanced beyond the distal tip of the guidewire and into and through the obstruction, or the operating head and guidewire may be advanced in tandem. Other methods that may be employed for guiding and steering the operating head include, but are not limited to, radio frequency systems, stereotactic systems, magnetic systems, remote control systems, and the like. The interventional catheters disclosed herein may be adapted for use with any of these steering systems.

The operating head is rotatable, incorporates cutter elements, and is operably connected to a rotatable and axially translatable drive shaft, drive system and control systems. In preferred embodiments, the operating head comprises at least one blade having a cutting surface that operates according to the principles of differential cutting. Although the "cutting" surfaces or blades of an interventional catheter of the present invention may be sharp and may actually "cut" material at the target site, the term "cut" or "cutting" or "cutter" or "blade(s)," as used herein, refers to cutting, scraping, abrading, ablating, macerating and otherwise breaking down undesired material into particles or smaller, removable, units of material. Cutter assemblies disclosed herein generally comprise a plurality of differential cutting blades and may incorporate fixed and/or adjustable blades as disclosed, for example, in U.S. Pat. Nos. 6,565,588 and 6,818,001, which are incorporated herein by reference in their entireties. Differential cutting blades are also disclosed, for example, in U.S. Patent Publication 2004/0006358 A1, which is incorporated herein by reference in its entirety. In some embodiments, the operating head may comprise an abrasive surface or an abrasive material provided on a surface of a rotational element.

In one embodiment, interventional catheters have an operating head incorporating a cutter assembly having a plurality of radially arranged, fixed blades, each blade providing a differential cutting surface at a leading edge. The term "leading" edge or surface, as used herein, indicates the edge or surface that contacts material during rotation of the operating head in a direction to achieve removal of material by contact with the edge or surface, and the term "trailing" edge or surface, as used herein, indicates the edge or surface generally "behind" or on an opposite side of the leading edge. In one embodiment, a fixed blade cutter assembly comprises a plurality of raised cutting surfaces having depressions between adjacent cutting surfaces, with both the blade and depression structures terminating in a generally smooth distal collar.

Cutter assemblies may optionally incorporate openings or ports providing access to an internal cavity communicating, for example, with a sealed lumen of the catheter for aspiration and/or infusion of fluids. Ports may be provided in a fixed blade or adjustable blade cutter assembly, or both. In a fixed blade cutter assembly, ports may be located between all or a portion of the cutting surfaces and are preferably provided in a radially symmetrical arrangement in a generally proximal portion of the cutter assembly. In alternative cutter assemblies, there are no ports or openings providing access to the interior of the cutter assembly.

The cutter assembly may comprise one or more cutters or cutting surfaces and one or more distinct types of cutter elements. For example, a dual cutter configuration incorporates a fixed diameter cutter and an adjustable diameter cutter in combination. Dual cutter assembly configurations are described in the prior art publications incorporated herein by reference and may present two different material removal profiles in two different operational modes. In one mode, the cutter assembly is rotated and advanced to remove occlusive material in an initial "pilot pass" in which the fixed diameter cutter is the primary cutter, and the adjustable diameter cutter is in a smaller diameter condition. Following one or more pilot passes, the adjustable diameter cutter may be adjusted to a larger diameter condition in a second mode of operation, and the dual cutter assembly may be advanced so that the adjustable diameter cutter, in its expanded condition, operates as the primary cutter and clears an even larger volume of occlusive material. Following this material removal operation, the adjustable diameter cutter may be adjusted to a smaller diameter condition and the dual cutter assembly may be withdrawn from the site. This method, using the material removal system of the present invention, obviates the need for the operator to remove and replace, or interchange, cutter assemblies during a material removal operation to provide cutters having different diameters and material removal capabilities.

According to one embodiment, fixed blade cutter assemblies of the present invention incorporate differential cutting surfaces having a leading edge cant angle of less than 90°, and preferably incorporate differential cutting surfaces having a leading edge cant angle of less than 80°. The trailing edge cant angle may be different from the leading edge cant angle, and is generally less than the leading edge cant angle. Fixed blade cutter assemblies may incorporate differential cutting surfaces having generally planar leading and trailing faces. In one embodiment, the generally planar differential cutting surfaces are continuous and generally smooth, and they do not provide any communication with internal spaces of the cutter assembly. In general, any number of blades, generally from about three to about twelve, may be provided in a radially symmetrical arrangement. In one illustrative embodiment, ten fixed cutter blades are provided in a cutter assembly having multiple ports providing access to an internal cavity. In another illustrative embodiment, four fixed cutter blades having smooth, continuous surfaces with no openings are provided.

Interventional catheters of the present invention incorporating a fixed blade cutter assembly may additionally comprise cutter blades presenting differential cutting surfaces having a different configuration, profile and/or cant angle. Additional cutter surfaces may be provided proximally to the fixed blade cutter assembly, for example, as adjustable (e.g., pivoting) cutting blades, as described in the patent publications incorporated herein by reference. Pivoting cutting blades may be mounted for limited rotation on a rotating structure with or without ports that communicate with an internal space for aspiration and/or infusion. In general, any number of blades, generally from about three to about twelve, may be provided in a radially symmetrical arrangement. According to one embodiment, adjustable blade cutter assemblies of the present invention may incorporate differential cutting surfaces having a leading edge cant angle of less than 100° and greater than 80°.

Cutter assemblies comprising an operating head having a combination of cutter blades and another material removal modality are also contemplated. In some embodiments, fixed or adjustable cutting blades may be provided in an operating head in combination with a non-cutting material removal system, such as a laser-based device, a high frequency ultrasound device, or a heating and/or electrically ablative device. The fixed or adjustable cutting blades may be positioned proximal to or distal to the non-cutting material removal system.

Cutter assemblies incorporating cutter surfaces having a stepped configuration are disclosed herein and are preferred for many applications. Stepped blades have a raised cutting surface or blade positioned adjacent a shoulder portion that is generally atraumatic to tissue. This blade configuration essentially limits the depth of tissue cut during rotation of the blade to the depth of the raised cutting surface. Both fixed and adjustable cutting blades may be provided with stepped cutting surfaces. More aggressive or less aggressive blades may be designed and provided, depending on the dimensions of the raised cutting surface, the cant angle of the cutting edge of the raised cutting surface, and the relative dimensions of the raised cutting surface, the width of the shoulder portion and other blade surface geometries. Suitable stepped cutter blade geometries may incorporate a leading edge cant angle of greater than 70°, more preferably greater than 80°, and in some embodiments between about 80° and 110°. These blades present a more aggressive leading cutting edge than blades having a lower cant angle, but they demonstrate a reduced and generally more benign cutting profile because the effective cutting edge is limited by the configuration of the cutting edge and the presence of the generally atraumatic shoulder portion.

In certain embodiments, the interventional catheters disclosed herein include an aspiration system for removal of debris from the intervention site via aspiration through one or more aspiration ports. Aspiration systems suitable for use in interventional catheters of the present invention are described, for example, in the patents incorporated herein by reference and in U.S. Patent Publication 2004/0220519 A1, which is also incorporated herein by reference in its entirety. Debris generated during a material removal operation is entrained in fluids (e.g. blood), and the aspirate fluid containing debris is removed by aspiration through material removal port(s) provided in proximity to the cutter assembly and withdrawn through a sealed lumen of the interventional catheter. The sealed lumen is connectable to an aspirate collection system.

Liquid infusion may be provided in, or in proximity to, the operating head. Infusion of liquids may be used to provide additional liquid volume for removal of debris, or to deliver lubricating fluids, treatment agents, contrast agents and the like. Infusion of fluids such as saline in proximity to the target material removal area may be desirable because it tends to reduce the viscosity of the materials being removed, thus facilitating removal through relatively small diameter lumens. Liquid infusion may be provided distal or proximal to the operating head, and/or may be provided through the operating head. Liquid infusion systems are well known in the art.

DETAILED DESCRIPTION

Certain preferred embodiments are described herein with reference to a material removal device having a rotational cutting head. It will be appreciated that this device embodiment is being described as illustrative and that the inventions and features disclosed herein are applicable to interventional catheters having different types of operating heads.

Figure 1:
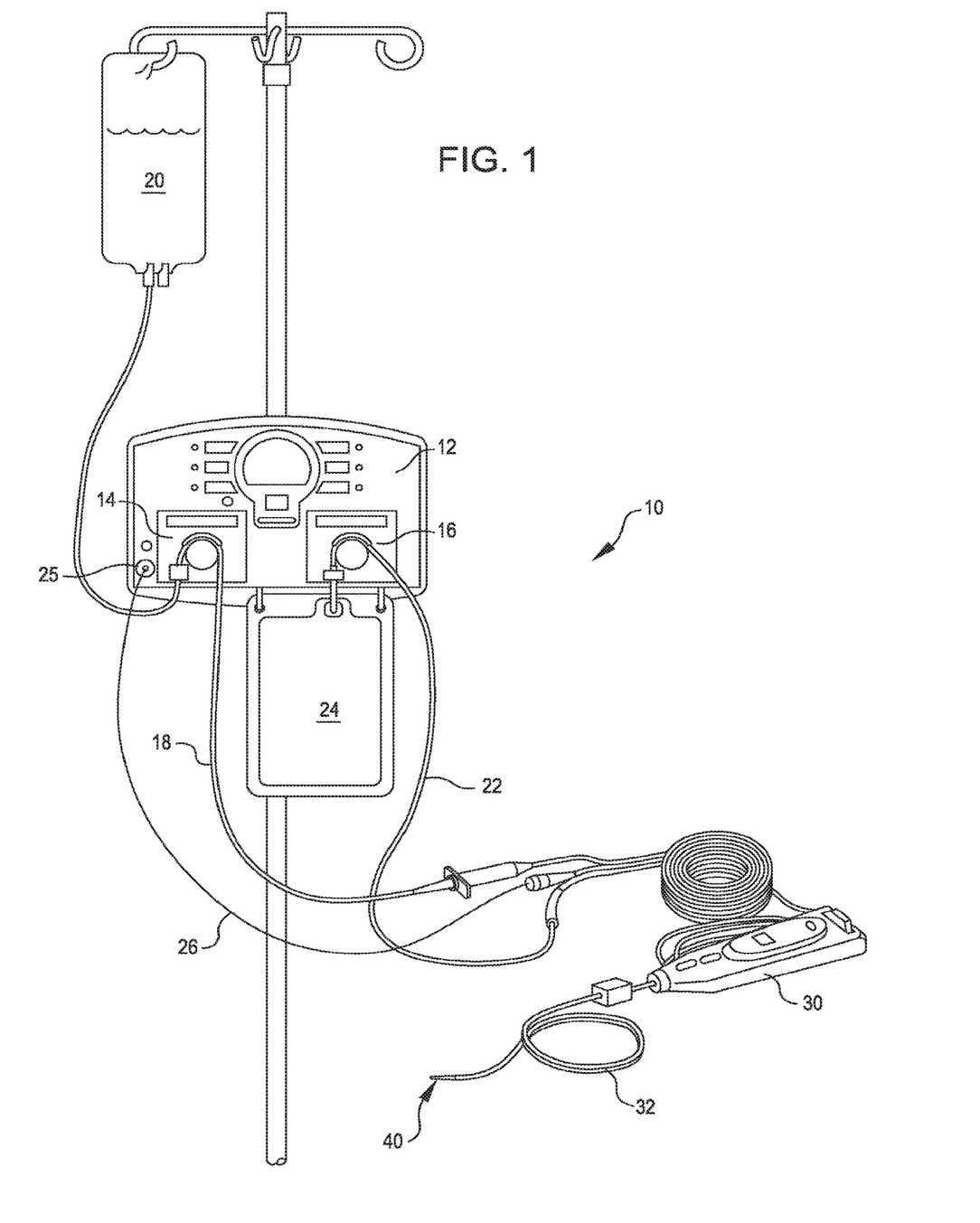
FIG. 1 is a schematic diagram of an interventional catheter assembly comprising an operating head mounted at or near a distal end of a catheter system, a controller and a console unit.

FIG. 1 illustrates an exemplary embodiment of an interventional catheter assembly 10 comprising console unit 12, controller 30, and catheter system 32 having a rotatable operating head 40 located at or in proximity to the distal end of the catheter system and incorporating one or more cutter assemblies. Controller 30 may be used to manipulate (e.g. advance and/or rotate) the catheter system 32 and operating head 40, or alternative controls may be provided. The configuration of the operating head and cutter assemblies will be described below with reference to FIGS. 2-7.

Console unit 12 may incorporate an infusion pump 14 and/or an aspiration pump 16. During operation of the interventional catheter, an infusate conduit 18 draws fluid from an infusate reservoir 20 and operably contacts the infusion pump 14 to provide fluid through an infusion lumen in catheter system 32 to one or more infusion ports provided in proximity to the operating head. Similarly, but in reverse, fluids with entrained particulates may be withdrawn from the site of intervention through an aspiration lumen in catheter system 32 and conveyed to aspiration conduit 22, which is in operable contact with the aspiration pump 16, and communicates with the aspirate collection vessel 24. Console unit 12 may also provide a power source for operating the operating head and system components, or it may be in communication with an external power source. In the illustrated embodiment, console unit 12 provides power to the interventional catheter assembly and controller 30 by means of a device power port 25 and power cord 26.

Various microprocessor, electronic components, software and firmware components may be provided within or in communication with the console unit for controlling operation of the interventional catheter as described herein. Software may be provided in a machine-readable medium storing executable code and/or other data to provide one or a combination of mechanisms to process user-specific data. Alternatively, various systems and components may be controlled using hardware or firmware implementations. Data storage and processing systems may also be provided in console unit 12.

One function of console unit 12 is to provide feedback of system and/or environmental conditions or operating parameters. The console unit may output operational information concerning operating conditions and feedback from the material removal site to the operator. According to one embodiment, console unit 12 provides continuously updated output to an operator of operating parameters such as operating head rotation rate, which may include the actual run speed as well as the desired speed; operating head advance rate; aspiration rate and/or volume; infusion rate and/or volume; elapsed run-time; and the like.

Certain automated and selectable control features may be implemented in console unit 12. Preset routines or programs involving various operating parameters may be preselected, stored and selectable by an operator, for example. Thus, according to one embodiment, the disclosed material removal system implements control features based on an operator's input of specified parameters. Specified parameters may include, for example: lesion length, lesion type and character, such as calcified, fibrotic, lipid/fatty and the like; historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, the control unit may calculate and implement automated operating conditions, such as: cutter assembly rotation rate and profile; cutter assembly advance rate and profile; aspiration rate and profile; infusion rate and profile; cutter assembly size; and the like. Various system operating parameters, operating conditions, patient conditions, and the like may also be recorded and stored during interventions to preserve a record of the patient and intervention operational parameters.

In one embodiment, console unit 12, together with aspiration pump 16 and infusion pump 14 and the associated control and display features, is provided as a separate, re-usable unit, that may be used as standard equipment in operating rooms, for example. In the system illustrated, console unit 12 is not contaminated by contact with blood or aspirate during operation, and the power and control systems are durable and long-lasting and may be reused for many interventions. Console unit 12 may be provided in a housing designed to sit on a platform during operation, or the housing may be designed for mounting on a portable structure, such as an i.v. pole or another structure. The interventional catheter system, comprising the catheter system 32 with operating head 40, controller 30, aspirate conduit 22, aspirate collection vessel 24, and infusion conduit 18 may be provided as a sterile, single use system kit.

The catheter system and operating head are described below with reference to a rotatable operating head employing a cutter assembly having a plurality of cutter blades for material removal. In interventional catheter applications incorporating aspiration and/or infusion systems, aspiration and/or infusion conduits terminate at or within controller 30, where they communicate with aspiration and infusion lumens within the catheter system 32. A rotatable drive shaft for driving the operating head is provided in catheter system 32. A guidewire may also transit controller 30 and catheter system 32. In general, controller 30 or an associated control mechanism provides user-operated mechanisms for rotating and/or translating the operating head. Controller 30, which is constructed from a durable, sterilizable material, such as hard plastic, may be provided in any convenient ergonomic design and constructed for placement in proximity to and/or in contact with the external body. In one embodiment, the controller may include an integrated handle for operator convenience in holding and supporting the controller during operation. Catheter system 32, exiting controller 30, is axially translatable with respect to controller 30 as the operating head and catheter system are guided to a target material removal site. It will be appreciated that some of the control and operational features described herein with reference to controller 30 may be provided in console unit 12 and, likewise, some of the control and operational features described with reference to console unit 12 may be provided in controller 30.

The operating head 40 of the interventional catheter disclosed herein may comprise any of a variety of rotational cutting devices or assemblies having one or more cutting surface(s) for cutting, fragmentizing, pulverizing, ablating, scraping, grinding or otherwise reducing the size of undesired material and/or separating undesired material from healthy tissue, such as the walls of a blood vessel, in proximity to the target removal site. Differential cutter assemblies may be provided, as described in the U.S. patent publications incorporated herein by reference. Operating heads comprising abrasive rotational surfaces may also be used. The operating head, or sub-components thereof, such as the cutting surfaces, may be coated with a radio-opaque material such as gold, platinum, inks and the like, to render the operating head radioscopically visible and to assist a medical professional in guiding and positioning the cutter assembly relative to an occlusion.

Exemplary materials for construction of the cutting surface(s) of cutter assemblies of the present invention include metals, metal alloys, ceramics and cermet materials such as, but not limited to, various types of stainless steels, such as series 300 and/or 400, vanadium steel, nickel-titanium, titanium, titanium-containing metals and oxide ceramics. Metallic materials such as stainless steels may be hardened using well-known techniques. In general, cutter surfaces are constructed from hard materials and may be treated to impart even greater hardness to the cutter surfaces.

Figure 2A:
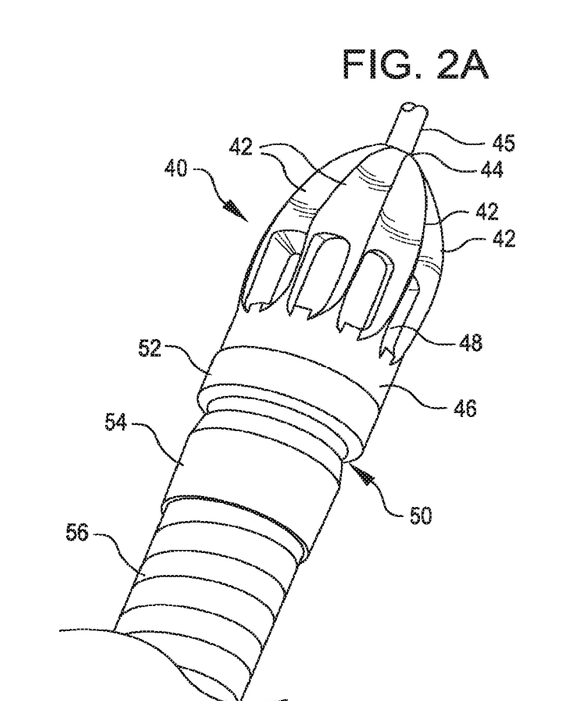
FIG. 2A is an enlarged perspective view of one embodiment of a fixed blade distal cutter assembly of the present invention.

FIG. 2A illustrates a fixed blade cutter assembly having a plurality of differential cutting surfaces according to the present invention. Cutter assembly 40 comprises a plurality of cutter blades 42 arranged in a radially symmetrical arrangement with respect to a central longitudinal axis of the cutter assembly. Each of the cutter blades 42 is joined at a distal end to form a distal bore 44 which serves as a rotating bearing for a guidewire 45. In cutter assemblies that are employed without guidance over a guidewire, cutter blades 42 may alternatively terminate at their distal ends in a blunt or rounded or pointed structure without forming a distal bore. Cutter blades 42 terminate at their proximal ends in a proximal ringlike collar 46.

In various types of interventional catheters, cutter assembly 40 may be mounted to a drive shaft, a catheter system, or an intermediate bearing structure. FIG. 2 illustrates an embodiment in which cutter assembly 40 is mounted to a rotating element 52 of bearing 50. A non-rotating element 54 of the bearing is mounted to a distal portion of catheter 56 or another cylindrical structure provided at a distal portion of the interventional catheter. The rotating bearing element and cutter assembly are rotated during operation by the drive shaft, while the non-rotating element of the bearing structure and the distal portion of the catheter remain stationary during rotation of the operating head.

The overall outer configuration of cutter assembly 40 is generally round from an axial view and oblong or frusto-conical from a profile view. The outer edges of cutter blades 42 taper along a curved line between smaller diameter distal bore 44 and larger diameter proximal collar 46, such that the diameter of the cutter assembly decreases toward its distal end. This configuration allows the smaller diameter distal end of the cutter assembly to penetrate an obstruction or partial obstruction while providing a progressively larger bore as the cutter assembly is advanced through the obstruction.

Each of the cutter blades 42 has a differential cutter surface on a leading edge 43 that contacts material to be removed when cutter assembly 40 is rotated during a material removal operation. Differential cutter surfaces may be optimized for use in different types of cutting environments, for different types of materials being removed, and for different applications, by providing different cant angles. In general, the higher the cant angle the more aggressive the action of the cutter surface. A cutter surface having a cant angle of less than 90° has previously been shown to be gentle and benign when it contacts a resilient surface, such as the wall of a body lumen, yet it effectively cuts and abrades less resilient materials, such as plaque, calcified material and thrombus, to provide effective removal of disease material. Cutter assemblies disclosed herein are benign to healthy, elastic tissue while providing effective removal of less elastic, disease tissue.

The leading edge cutter surfaces are preferably generally smooth, although they may be provided as abrasive surfaces, or surfaces coated with abrasive materials, in alternative embodiments. The use of diamond grit or other types of abrasives on the cutting surfaces may reduce the size of particles generated during rotation of cutter assemblies, thereby improving the efficiency of removal of the particles and reducing the risk of undesirable side effects. The use of diamond grit or other types of abrasives is particularly advantageous when removing hard materials, and/or small, targeted areas of unwanted material. The diamond grit or other type of abrasive employed on the cutting surfaces may have a particle size of about 400 microns or less. In some embodiments, the abrasive materials have a particle size of about 100 microns or less, while in some embodiments, the abrasives have a particle size of about 40 microns or less, generally between about 20 and 40 microns in size.

Figure 2B:
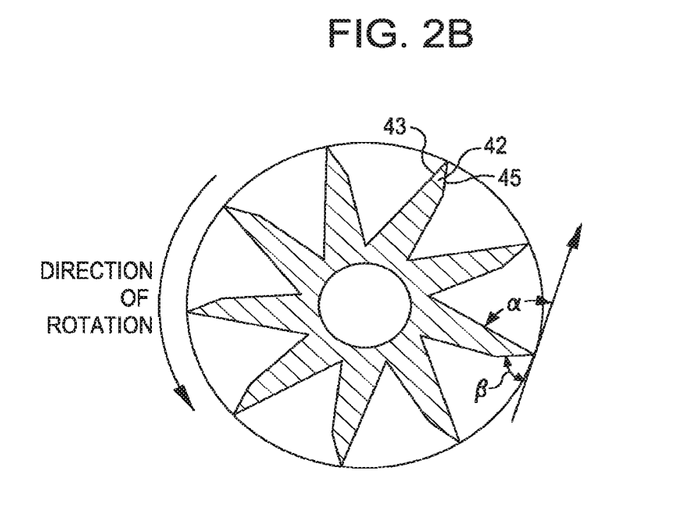
FIG. 2B is a cross-sectional view, illustrating the leading edge cutter surface cant angles for the differential cutter blades of the cutter assembly of FIG. 2A.

The cant angle $\alpha$ formed by the leading edges 43 of cutter blades 42 and a line tangent to a circle circumscribing the outer edges of the cutter surfaces are illustrated in FIG. 2B. Cant angles $\alpha$ formed by leading edges 43 of cutter surfaces 42 are preferably less than 90°. In some embodiments of fixed blade cutter surfaces disclosed herein, the cant angle of the cutter blades is less than 80° and, in some embodiments, is about 70°. Trailing angles β formed by trailing edges 45 of cutter surfaces 42 are preferably less than the corresponding cant angles and, in many embodiments, are less than 70°.

The number of cutter blades provided on a fixed cutter assembly of the present invention may vary depending on the interventional application and the nature of the material being removed. As few as three blades may be provided and as many as 12-15 blades may be provided in a radially symmetrical arrangement. Fixed blade cutter assemblies having 7 or more blades are preferred for many applications. In one embodiment, as illustrated in FIG. 2A, a plurality of generally oval ports 48 may be provided between neighboring blades for communication with an internal space of the cutter assembly. Ports 48 may be provided between each pair of neighboring blades, as illustrated, or fewer ports may be provided. In one embodiment, as illustrated, ports 48 are preferably provided in a proximal portion of the cutter assembly in proximity to the proximal collar. Ports 48 may be used as aspiration or infusion ports and communicate with an appropriate aspiration or infusion lumen provided within catheter 56. Additional aspiration and/or infusion ports may be provided in locations proximal to the cutter assembly.

Figure 3:
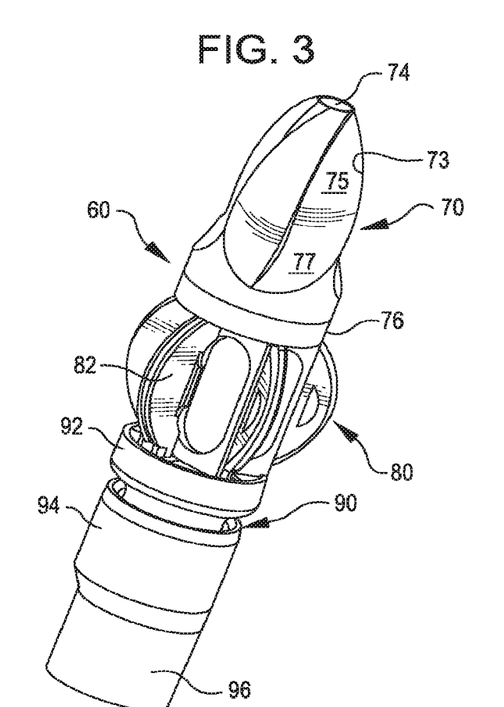
FIG. 3 is an enlarged perspective view of a dual cutter assembly of the present invention having a distal fixed blade assembly and a proximal adjustable blade assembly.

FIG. 3 illustrates another cutter assembly for interventional catheters of the present invention in which a dual cutter assembly 60 comprises a fixed blade cutter 70 and an adjustable blade cutter assembly 80. In various types of interventional catheters, cutter assembly 60 may be mounted to a drive shaft, a catheter system, or an intermediate bearing structure. FIG. 3 illustrates an embodiment in which cutter assembly 60 is mounted to a rotating element 92 of bearing 90. A non-rotating element 94 of the bearing is mounted to a distal portion of catheter 96 or another cylindrical structure provided at a distal portion of the interventional catheter. The rotating bearing element 92 and cutter assembly 60 are rotated during operation by the drive shaft, while the non-rotating element of the bearing structure 94 and the distal portion of the catheter 96 remain stationary during rotation of the operating head.

Figure 4:
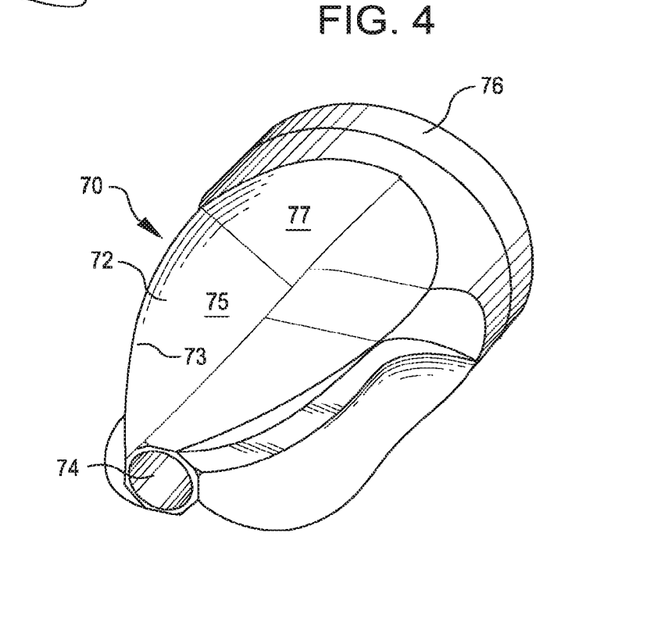
FIG. 4 is an enlarged perspective view of the fixed blade cutter assembly illustrated in FIG. 3.

Fixed blade cutter assembly 70, illustrated in isolation in FIG. 4, comprises a plurality of differential cutting surfaces 72. The overall outer configuration of cutter assembly 70 is generally round from an axial view and oblong or frustoconical from a profile view. The outer edges of cutter blades 72 taper along a curved line between smaller diameter distal bore 74 and larger diameter proximal collar 76, such that the diameter of the cutter assembly decreases toward its distal end. This configuration allows the smaller diameter distal end of the cutter assembly to penetrate an obstruction or partial obstruction while providing a progressively larger bore as the cutter assembly is advanced through the obstruction.

Each of the cutter blades 72 is fixed on the cutter assembly and preferably has a differential cutter surface on a leading edge 73 that contacts material to be removed when cutter assembly 70 is rotated during a material removal operation. The leading edge cutter surfaces are preferably generally smooth, although they may be provided as abrasive surfaces, or surfaces coated with abrasive materials, in alternative embodiments. The blades may be provided as generally planar surfaces 75 at a distal portion, terminating proximally in a curved or scooped area 77. The cant angles formed as described above by the leading edges 73 of cutter surfaces 72 and a line tangent to a circle circumscribing the outer edges of the cutter surfaces at each cutter surface are preferably less than 90°. In some embodiments of fixed blade cutter surfaces disclosed herein, the cant angle of the cutter blades is less than 80° and, in some embodiments, is about 70°. The trailing angles β formed by the trailing edges 78 of cutter surfaces 72 and a line tangent to a circle circumscribing the edges of the cutter surfaces are generally less than the cant angle α and, in many embodiments, are less than 70°.

The fixed blade cutter assembly 70 does not have ports or openings, other than the guidewire bore 74, communicating with an interior of the assembly. Aspiration and/or infusion ports may be provided elsewhere in proximity to the cutter assembly, if desired. The number of cutter blades provided on fixed cutter assembly 70 of the present invention may vary depending on the interventional application and the nature of the material being removed. As few as three blades may be provided and as many as 5-7 blades may be provided in a radially symmetrical arrangement. Fixed blade cutter assemblies having 3 or more blades are preferred for many applications.

Cutter assembly 60 illustrated in FIG. 3 also incorporates an adjustable blade cutter assembly 80 having a plurality of cutter surfaces 82 presenting a different cutting profile than that of cutter surfaces of the distal blades 72. Many different types of adjustable blade cutter assemblies are known in the art and may be used in combination with a fixed blade distal cutter assembly of the present invention. Cutter assembly 80 may comprise a plurality of pivoting blades, for example, that move between a tangential, non-cutting, position and a radial, cutting, position by changing the direction of rotation of the cutter assembly. The fixed blade cutter assembly may be operated in one direction of rotation in a first cutting operation to clear a passageway, and the adjustable blade cutter may be operated in an opposite direction of rotation in a second cutting operation to clear a larger opening in a lumen or cavity. Cutter assemblies of this type are described in the patent publications incorporated herein by reference.

Figure 5A:
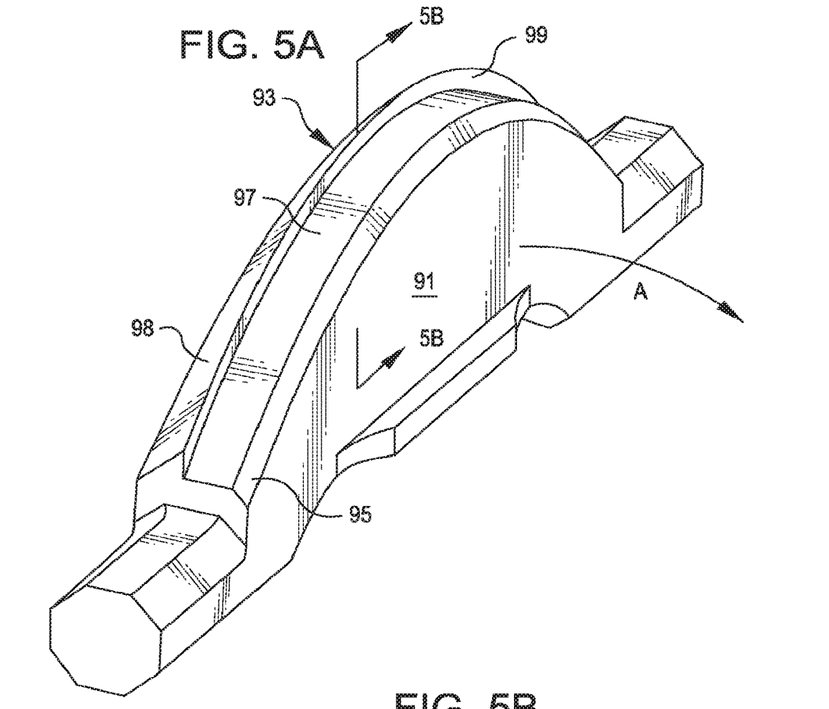
FIG. 5A is an enlarged perspective view of a stepped cutter blade of the present invention.
Figure 5B:
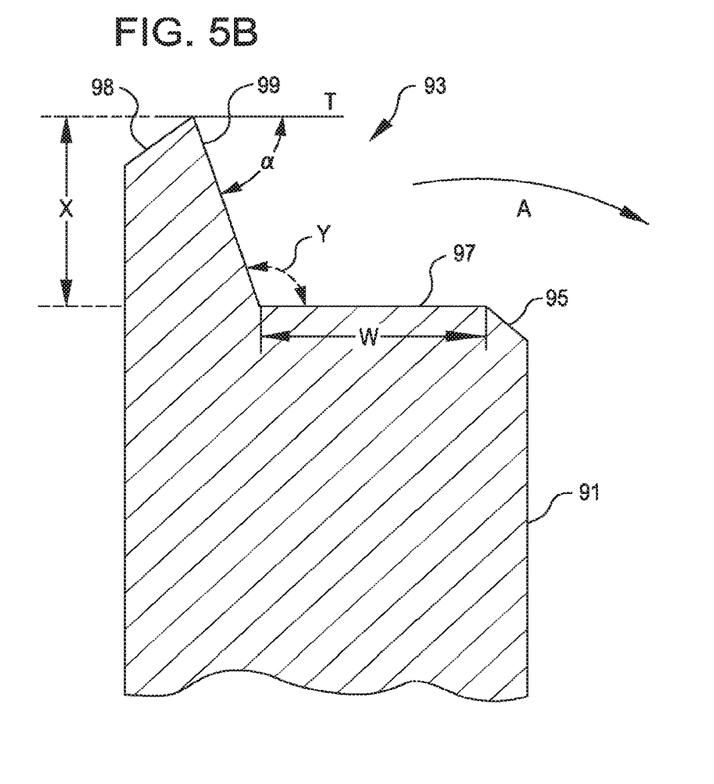
FIG. 5B is an enlarged cross-sectional view of the stepped blade of FIG. 5A taken through line 5B-5B.

FIGS. 5A and 5B illustrate a stepped cutter blade configuration that may be incorporated in cutter assemblies of the present invention. While cutter blade 93 is illustrated as a generally fan-shaped, flat blade suitable for use, for example, in an adjustable blade cutter assembly, it will be appreciated that the stepped blade cutter configuration may be incorporated in cutter blades having a variety of configurations, including fixed cutter blades and different configurations of adjustable cutter blades. Cutter blade 93 illustrated in FIGS. 5A and 5B is designed to rotate in a clockwise direction A. Cutter blade 93 has a leading edge cutting surface 99 adjacent or in proximity to a shoulder region 97 and a trailing surface 98. An angled or chamfered surface 95 may be provided between shoulder region 97 and the leading surface 91 of the cutter blade. As cutter blade 93 rotates in clockwise direction A, the leading surface 91 or chamfered edge 95 of blade 93 contacts the tissue first, followed by the shoulder 97 and cutter surface 99. The leading surface 91, chamfered edge 95 and shoulder 97 are generally atraumatic to tissue, while cutter surface 99 exerts a material removal action. Cutter surface 99 preferably forms a cant angle α of from about 60° to about 110°, more preferably from about 70° to about 100°, and more preferably yet from about 80° to about 95°, with respect to a line T tangent to the circumscribed arc of the circumference of the cutter assembly.

The height "X" of the cutter surface 99 from its outer edge to the point where it joins shoulder 97 is one factor that governs the "aggressiveness" of the cutter blade. For a given cant angle α, a shorter cutter surface X removes generally less material per pass than a longer cutter surface X. For many atherectomy and thrombectomy applications, cutter surface X may have a height X of from about 0.0005 to 0.010 inch, with heights of from about 0.001 to 0.003 inch being especially preferred. The height X may be substantially uniform along the length of the cutter surface, or it may taper along the length of the cutter assembly. In general, the cutter surfaces provided on a cutter assembly have the same or a similar cant angle and height X, but when multiple cutter assemblies are provided, the cant angles and heights X of cutter blades provided on the different cutter assemblies may be varied to vary the cutting properties of the assemblies.

Shoulder region 97 is provided adjacent or in close proximity to cutter surface 99 and may have a substantially flat profile, or an angled or curved profile. The angle "Y" formed by the plane of cutter surface 99 and shoulder 97 is preferably from about 45° to about 150°, more preferably from about 60° to about 120°, and more preferably yet from about 80° to about 110°. The width "W" of shoulder region 97 is preferably greater than the height X of cutter surfaces 99. In one embodiment, the width W of shoulder region 97 is from about 1.5 to about 10.0 times the height X of cutter surface 99; in another embodiment the width W of shoulder region 97 is from about 2.0 to about 4.0 times the height X of cutter surface 99. For atherectomy and thrombectomy applications, the width W of shoulder 97 is preferably from about 0.001 to about 0.015 inch, and the width W of shoulder 97 is more preferably from about 0.003 to about 0.010 inch.

Optional chamfered surface 95 may be provided as an angled or curved surface between the leading blade surface 91 and shoulder 97. Chamfered surface 95 is generally narrower than shoulder 97 and may have a constant width over its length, or it may taper from one end to another, or toward and away from a central blade portion. Chamfered surface 95 and shoulder 97 contact and displace the surface of tissue prior to contact between the tissue surface and the cutting surface 99, thereby restricting the depth of the "bite" that cutter surface 99 takes in the tissue and reducing the risk of damage to tissue. The protective effect of chamfered surface 95 and shoulder 97 enables the use of cutting surfaces having more aggressive cant angles, for example cant angles of about or greater than 80°, in order to effectively cut hardened disease material, while providing protection to healthy elastic tissue.

Cutter blades 93 may additionally be provided with cut-outs or cavities that penetrate their surfaces in locations that are radially inward of the cutter surfaces and shoulders. In one embodiment, a curved slot having a curve that substantially matches the outer edge of the cutter surface may be provided, for example, to reduce drag produced by rotation of the blade against fluids. In another embodiment, multiple slots or openings may be provided through the surface of cutter blades 93. In general, the slots or openings represent at least about 5% of the surface area of the blade surface and more typically represent at least about 10% to 15% of the surface area of the blade surface. Slots or openings provided in the cutter blade surfaces generally represent less than about 50%> of the blade surface area.

Figure 6:
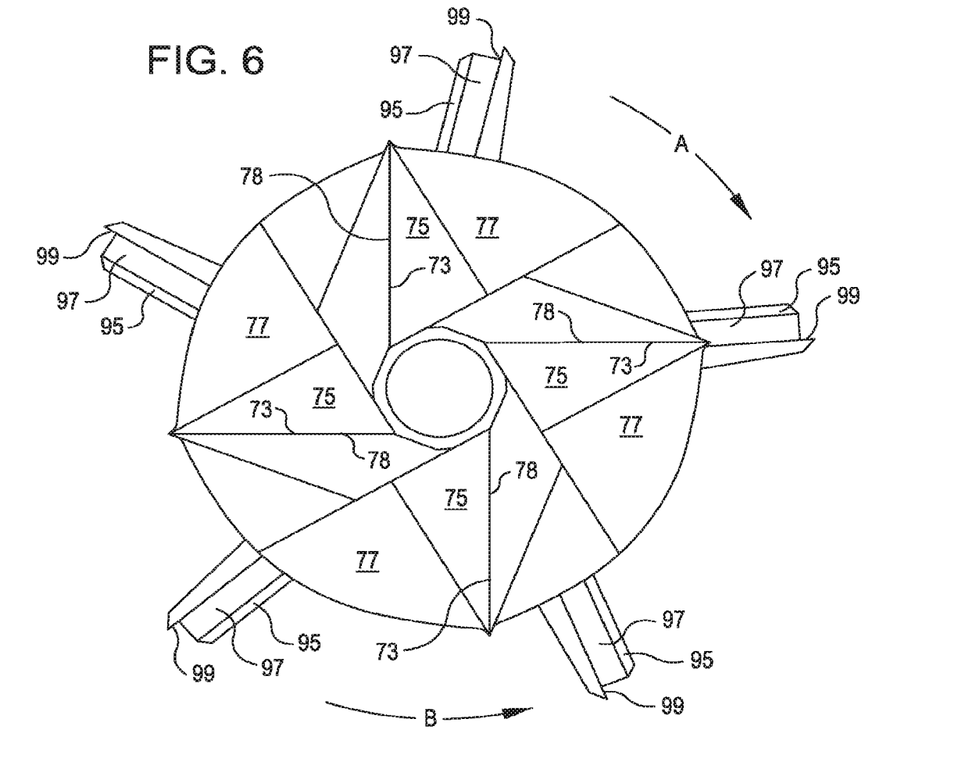
FIG. 6 is an enlarged schematic end view of a cutter assembly incorporating a distal fixed blade cutter assembly as shown in FIG. 4 and an adjustable blade cutter assembly employing stepped cutter blades as illustrated in FIGS. 5A and 5B.

FIG. 6 illustrates an end view of an operating head of the type illustrated in FIG. 3 having a distal cutter assembly of the type illustrated in FIG. 4 and a proximal cutter assembly having stepped blades of the type illustrated in FIGS. 5A and 5B. The fixed and adjustable blade cutter assemblies provide different cutting profiles and operate in opposite directions of rotation of the operating head. The distal fixed cutter 70 operates as the primary cutter assembly when the operating head is rotated in clockwise direction A. Leading blade surfaces 73 provided at the edges of leading blade faces 75 do not have a stepped configuration and preferably have cant angles α of less than about 80°, generally from about 65° to about 90°. Trailing blade surfaces 78 preferably have cant angles of less than that of the leading blade faces. Proximal cutter assembly surfaces 77 preferably have a curved or scooped configuration, which is not apparent from the figure.

Proximal blades 93 have a stepped cutter surface configuration and operate as the primary cutters when operating head 60 is rotated in counterclockwise direction B. Stepped cutter blades 93 present a cutter surface 99 adjacent shoulder 97, and chamfered edge 95 is presented as a leading surface. When the operating head of FIG. 6 is rotated in counterclockwise direction B, tissue is contacted first by chamfered edge 95 (and, to some degree, the leading blade surface positioned radially inwardly from chamfered edge 95) and shoulder 97, which present substantially atraumatic surfaces, and stepped cutter surfaces 99 operate as the primary cutter surfaces. Cutter blades 93 preferably assume a general tangential orientation when the operating head is rotated in clockwise direction A, as disclosed in the patent publications incorporated herein by reference.

Figure 7:
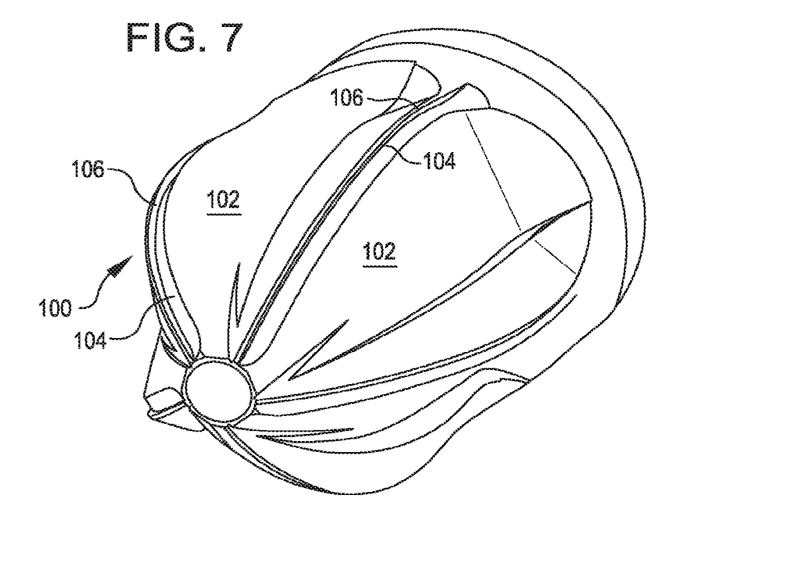
FIG. 7 is an enlarged perspective view of another stepped blade configuration of the present invention.

Stepped cutter blades of the present invention may be provided on a variety of fixed and adjustable cutter blades, and on fixed and adjustable cutter assemblies. An enlarged view of a fixed blade cutter assembly similar to that described with reference to the cutter assembly of FIG. 4 is shown in FIG. 7. In this embodiment, cutter assembly 100 has a plurality of cutter blades 102 oriented for operation by rotation in a counterclockwise direction B. Cutter blades 102 incorporate upstanding cutter surfaces 106 adjacent shoulders 104. The embodiment illustrated in FIG. 7 does not incorporate a chamfered edge, but the shoulders 104 provide generally atraumatic contact with tissue. The trailing edges of cutter blades 102 may be provided at a shallow angle to cutter surfaces 106, providing a relatively blunt circumferential edge on cutter blades 102.

It will be recognized that the operating heads, cutter assemblies and differential cutting surfaces disclosed herein may be incorporated in interventional catheters having different types of power, display and control systems, from those described herein. The differential cutting surfaces disclosed herein may be incorporated in any type of interventional catheter that may be employed for removal of undesired material located within a human or animal body. While the present invention has been described with reference to specific embodiments and figures, these specific embodiments should not be construed as limitations on the scope of the invention, but merely as illustrations of exemplary embodiments. It is further understood that many modifications, additions and substitutions may be made to the described interventional catheter and control system without departing from the scope of the present invention.

What is claimed is:

1. A method for removal of obstructive material from a target site in a body lumen, comprising:
    rotating an operating head connected to a distal end of a rotatable drive shaft in a first rotational direction such that a plurality of first leading edge cutting surfaces ablate obstructive material at the target site; and
    rotating the operating head in a second rotational direction opposite the first rotational direction such that a plurality of second leading edge cutting surfaces ablate obstructive material at the target site;

wherein the plurality of second leading edge cutting surfaces ablate the obstructive material at a greater rate than the plurality of first leading edge cutting surfaces;
wherein the operating head includes a plurality of cutting blades, wherein the plurality of second leading edge cutting surfaces are located on the plurality of cutting blades,
wherein each of the plurality of cutting blades includes a shoulder region atraumatic to tissue,
wherein the shoulder region restricts how far the plurality of second leading edge cutting surfaces cut into the obstructive material.

2. The method of claim 1, wherein the operating head includes a fixed diameter cutter and an adjustable diameter cutter.

3. The method of claim 2, wherein the fixed diameter cutter includes the plurality of first leading edge cutting surfaces and the adjustable diameter cutter includes the plurality of second leading edge cutting surfaces.

4. The method of claim 1, wherein the plurality of first leading edge cutting surfaces are coated with an abrasive material.

5. The method of claim 4, wherein the abrasive material is diamond grit having a particle size of 400 microns or less.

6. The method of claim 4, wherein the abrasive material is diamond grit having a particle size of 100 microns or less.

7. The method of claim 1, wherein the plurality of first leading edge cutting surfaces are located distal of the plurality of second leading edge cutting surfaces.

8. The method of claim 1, wherein the plurality of first leading edge cutting surfaces extend to an outer edge of the operating head, wherein a cant angle formed by the each of the plurality of first leading edge cutting surfaces and a line tangent to a circle circumscribing the outer edge of the operating head is less than 80 degrees.

9. The method of claim 8, wherein the plurality of second leading edge cutting surfaces extend to the outer edge of the operating head, wherein a cant angle formed by the each of the plurality of second leading edge cutting surfaces and a line tangent to a circle circumscribing the outer edge of the operating head is greater than 80 degrees.

10. The method of claim 1, wherein the plurality of second leading edge cutting surfaces extend to an outer edge of the operating head, wherein a cant angle formed by the each of the plurality of second leading edge cutting surfaces and a line tangent to a circle circumscribing the outer edge of the operating head is between 80 degrees and 110 degrees.

11. The method of claim 1, wherein obstructive material is contacted first by the shoulder region prior to contacting the plurality of second leading edge cutting surfaces while rotating the operating head in the second rotational direction.

12. The method of claim 1, wherein the shoulder region has a width greater than a height of the plurality of second leading edge cutting surfaces.

13. A method for removal of obstructive material from a target site in a body lumen, comprising:
rotating an operating head connected to a distal end of a rotatable drive shaft in a first rotational direction such that a plurality of first leading edge cutting surfaces ablate obstructive material at the target site, the plurality of first leading edge cutting surfaces being coated with an abrasive material for initially contacting the obstructive material when the operating head is rotated in the first rotational direction; and
rotating the operating head in a second rotational direction opposite the first rotational direction such that a plurality of second leading edge cutting surfaces ablate obstructive material at the target site;
wherein the abrasive material is on trailing surfaces of the operating head when the operating head is rotated in the second rotational direction;
wherein the obstructive material is ablated at a greater rate in the second rotational direction than in the first rotational direction,
wherein the operating head includes a plurality of shoulder regions restricting how far the plurality of second leading edge cutting surfaces cut into the obstructive material in the second rotational direction.

14. The method of claim 13, wherein the plurality of first leading edge cutting surfaces extend to an outer edge of the operating head, wherein a cant angle formed by the each of the plurality of first leading edge cutting surfaces and a line tangent to a circle circumscribing the outer edge of the operating head is less than 80 degrees.

15. The method of claim 14, wherein the plurality of second leading edge cutting surfaces extend to the outer edge of the operating head, wherein a cant angle formed by the each of the plurality of second leading edge cutting surfaces and a line tangent to a circle circumscribing the outer edge of the operating head is greater than 80 degrees.

16. The method of claim 13, wherein the operating head includes a fixed diameter cutter and an adjustable diameter cutter, wherein the fixed diameter cutter includes the plurality of first leading edge cutting surfaces and the adjustable diameter cutter includes the plurality of second leading edge cutting surfaces.

17. A method for removal of obstructive material from a target site in a body lumen, comprising:
rotating an operating head connected to a distal end of a rotatable drive shaft in a first rotational direction such that a plurality of first leading edge cutting surfaces ablate obstructive material at the target site; and
rotating the operating head in a second rotational direction opposite the first rotational direction such that a plurality of second leading edge cutting surfaces ablate obstructive material at the target site;
wherein the plurality of second leading edge cutting surfaces ablate the obstructive material at a greater rate than the plurality of first leading edge cutting surfaces,
wherein the operating head includes a plurality of cutting blades,
wherein the plurality of second leading edge cutting surfaces are located on the plurality of cutting blades,
wherein each of the plurality of cutting blades includes a shoulder region atraumatic to tissue,
wherein obstructive material is contacted first by the shoulder region prior to contacting the plurality of second leading edge cutting surfaces while rotating the operating head in the second rotational direction.

18. The method of claim 17, wherein the shoulder region has a width greater than a height of the plurality of second leading edge cutting surfaces.

19. The method of claim 17, wherein the plurality of first leading edge cutting surfaces extend to an outer edge of the operating head, wherein a cant angle formed by the each of the plurality of first leading edge cutting surfaces and a line tangent to a circle circumscribing the outer edge of the operating head is less than 80 degrees.

20. The method of claim 19, wherein the plurality of second leading edge cutting surfaces extend to the outer edge of the operating head, wherein a cant angle formed by the each of the plurality of second leading edge cutting surfaces and a line tangent to a circle circumscribing the outer edge of the operating head is greater than 80 degrees.

* * * * *